United States Patent
Coppen

(12) 
(10) Patent No.: US 6,191,133 B1
(45) Date of Patent: *Feb. 20, 2001

(54) TREATMENT OF DEPRESSION AND PHARMACEUTICAL PREPARATIONS THEREFOR

(75) Inventor: Alec James Coppen, Epsom (GB)

(73) Assignee: Scarista Limited, Douglas (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/104,148

(22) Filed: Jun. 24, 1998

(51) Int. Cl.[7] .................... A61K 31/495; A61K 31/50; A61K 31/445; A61K 31/34

(52) U.S. Cl. .................... 514/249; 514/253; 514/321; 514/469; 514/640; 514/649; 514/651; 514/657

(58) Field of Search .................... 514/249, 649, 514/651, 640, 321, 657, 469, 253

(56) References Cited

U.S. PATENT DOCUMENTS 5,470,846   11/1995   Sandyk ................................. 514/159
5,538,734 *  7/1996   Le Grazie ............................ 424/436

FOREIGN PATENT DOCUMENTS 2072504   10/1981   (GB) .

WO97/38694   10/1997   (WO) .

OTHER PUBLICATIONS

Fava et al, Biological Abstracts, vol. 97, abstract No. 171609, 1997.*
Alpert and Fava, Medline Abstracts, abstract No. 97356217, 1997.*
Alpert et al, Derwent Drug File Abstracts, abstract No. 96–48268, 1996.*
Guaraldi et al, Embase Abstracts, abstract No. 93210920, 1993.*
Chemical Abstract Accession No. 1998:434420 & Dev. Cardiovasc. Med., 1997, 196 (Homocysteine Metabolism: From Basic Science to Clinical Medicine), 117–126 (T. Bottiglieri) "Folate, Vitamin B 12 and Neuropsychiatric Disorders".

* cited by examiner

Primary Examiner—William R. A. Jarvis
(74) Attorney, Agent, or Firm—Darby & Darby

(57) ABSTRACT

It has been found that the treatment of depression using known serotonin reuptake inhibitors (SRIs) and noradrenaline reuptake inhibitors (NRIs) may be improved by the administration therewith of folic acid or a precursor which produces folate in the patient. The daily dose of NRI or SRI is as prescribed for treatment of depression in the usual way. The daily dose of the folic acid or precursor should be such as to provide a folate dosage of 300–5000 micrograms/day.

11 Claims, No Drawings

TREATMENT OF DEPRESSION AND PHARMACEUTICAL PREPARATIONS THEREFOR

FIELD OF THE INVENTION

This invention relates to the treatment of depression, and to pharmaceutical preparations for use therein.

BACKGROUND TO THE INVENTION

Depression is one of the most important health care problems, especially in developed countries. At some time in their lives, about 5–10% of the population goes through a major depressive illness while minor depressive episodes may affect 25% or more of the population. The World Health Organisation has estimated that depression causes more global distress than any other illness.

Depression seriously disrupts people's lives, rendering existence both at home and at work difficult. Depression is the commonest reason for suicide. Depression is also associated with other illnesses, particularly cardiovascular diseases. People with a history of major depression were over four times more likely to have a myocardial infarction than normal individuals, even after allowing for known coronary disease risk factors (L A Pratt et al, Circulation 1996; 3123–3129). After a myocardial infarction, people with major depression are 3.5 times more likely to die than those who are not depressed (N Frasure-Smith et al, JAMA 1993; 1819–1825). There is therefore a particular need for effective treatments for depression which may be applied in particular to people with cardiovascular problems.

Depression has been treated in recent years usually by the combination of antidepressants selected from one of three major groups of compounds. These are the tricyclic and tetracyclic antidepressants and related compounds ("tricyclics"); the monoamine oxidase inhibitors (MAOIs); and the selective or partially selective serotonin uptake inhibitors (SRIs). The tricyclics have many and complex mechanisms of action, and are associated with many side effects, including cardiovascular side effects and toxicity such that they can be used for suicide attempts. The MAOIs inhibit one of the main enzymes involved in the degradation of catecholamines and also can have many side effects. Both the tricyclics and the MAOIs must be used with great caution in patients with cardiovascular disease. The SRIs have a relatively more selective action in inhibiting the reuptake of serotonin by nerve terminals and usually have fewer side effects than the other groups. However, almost as many patients on the new SRI antidepressants drop out of clinical studies due to adverse events as did with the older tricyclic drugs (K R Abrams, British Medical Journal, 1998; 316: 1183–4). Very recently, a further group of compounds known as noradrenaline reuptake inhibitors (NRIs), which constitute a new class of antidepressants, have been approved for general chemical use.

Although all four classes of antidepressants undoubtedly work, many patients fail to respond. For example, 30–40% of patients fail to respond to tricyclics (R J Bielski and R O Friedel, Archives of General Psychiatry 1976; 33: 1479–89). Failure rates with the MAOIs are similar or greater. Even the new SRIs are only modestly effective with as many as 40% of patients failing to respond in well controlled trials (e.g. S P Roose et al JAMA 1998; 279: 287–291). There is therefore a major need to improve the treatment of depression in view of its high personal and economic cost, both to the individual and to the society, particularly for patients with or at risk of cardiovascular disease. This improvement should include both better efficacy and reduced risk of adverse events.

Folic acid is an essential B group vitamin. Its Recommended Daily Allowance (RDA) in the USA is 200 microg for men and 180 microg for women. Women expecting to conceive are now recommended to take 400 microg/day in order to reduce the risk of spina bifida.

Folic acid is found in a number of natural forms which have pteroylglutamic acid as their common structure. In the gut wall, these are converted to methyltetrahydrofolic acid (MTHF) which is the main form of the vitamin in the blood. MTHF has a range of biological actions, but the most important is probably its interaction with homocysteine. Under the influence of the enzyme MTHF reductase, MTHF donates a methyl group to homocysteine in order to convert it to methionine which can then be used in a wide range of important methylation reactions. In the presence of inadequate supplies of folic acid, homocysteine levels become elevated. Homocysteine is associated with cardiovascular toxicity and there is increasing evidence that low folate levels may lead to elevated homocysteine levels which in turn lead to myocardial infarction and other forms of cardiovascular pathology (P Verhoef et al, Current Opinion in Lipidology 1998; 9: 17–22). Recent evidence suggests that homocysteine levels fall to a stable level in many people only at folic acid intakes of 400 microg/day or more (J Selhub et al, Journal of Nutrition, 1996; 126: 12585–655): P Verhoef et al, American Journal of Epidemiology 1996; 143: 845–59). The Recommended Daily Allowance may therefore be rather too low, especially for those at risk of cardiovascular disease.

This is likely to be particularly true of those individuals who carry a common mutation for the MTHF reductase gene. This is associated with somewhat reduced enzyme activity and a higher requirement for folate. The genetic variant is common, with European, American and Asian populations having prevalence rates for the homozygous mutation of 8–15%. Thus, a substantial proportion of the population is likely to require higher levels of folate than previously thought (P Verhoef et al, Current Opinion in Lipidology 1998; 9: 17–22: S S Kang et al, Circulation 1993; 88: 1463–9: P Frosst et al, Nature Genetics 1995; 10: 111–113).

Subnormal intakes and/or blood levels of folic acid have long been known to be associated with depression, although it is not clear whether this association is causal or not (T Bottiglieri, Nutrition Reviews 1996; 54: 382–290: J E Alpert and M Fava, Nutrition Reviews 1997; 55: 145–9). Most depressed people have reduced appetite and eat inadequately and so it is possible that depression in some individuals might cause folate deficiency. A possible mechanism whereby folate deficiency could cause depression is the influence of folate on the synthesis and release of neurotransmitters, particularly serotonin, but also including noradrenaline and dopamine. In animals made folate deficient, there is reduced brain serotonin synthesis (M Botez et al Nature 1979; 278: 182–3). The same paper showed that there is a window of folate intake within which serotonin synthesis is optimum. Increased amounts of folate as well as folate deficiency both suppressed the production of brain serotonin. Finding that folate in humans where folic acid is effective but not toxic is important.

Based on some of the earlier work, Coppen suggested that the addition of folic acid might enhance the effects of tricyclics and MAOIs and lithium (A J Coppen, UK Patent Application GB 2072504A, 1980). Coppen pointed out that in view of the work of Botez et al, both too low and too much folic acid might be associated with depression. He therefore emphasised that too much folic acid should not be given and on these grounds in his patent specification he claimed combinations of tricyclics, MAOIs or lithium with amounts of folic acid which were above 100 microg/day but below 300 microg/day. Higher amounts were specifically excluded because of the possibility of adverse effects.

As far as we are aware, only two studies have been published in which folic acid was investigated in a placebo-controlled trial as an adjunct to antidepressive treatment as suggested by Coppen. One of these, by Coppen himself, compared the effects of 200 microg/day folic acid of placebo as an adjunct to lithium in the prevention (not the treatment) of depression. There was a small reduction in the Beck depression scale in the folate, but not the placebo group, although the difference between the groups was not statistically significant (A J Coppen et al, Journal of Affective Disorders, 1986; 10: 9–13).

The other study researched the effect of MTHF administered at very high doses (15,000–90,000 microg/day) with the concomitant administration of any other antidepressant. In that study, 11 patients with depression who were also being treated with tricyclics or lithium were given 15,000 microg/day of MTHF, while 13 patients who were being treated with tricyclics or MAOIs were given placebo. After 3 and 6 months, the improvement in the folic acid group was greater than that of placebo. However, in the folic acid group, both serum and red cell folate concentrations were above the upper limit of the assay, suggesting that this dose of MTHF was excessive and possibly dangerous (P S A Godfrey et al, Lancet 1990; 336: 392–5).

Literature research reveals other studies in which MRHF at high dosage rates has been tested for its effects in depression. In senile depression, both MTHF (50,000 microg/day) and trazodone produced small (around 15%) reductions in depression as measured by the Hamilton Depression Rating Scale (HDRS). In an open study in elderly patients, 50,000 microg/day was associated with a substantial improvement in depression, but without a placebo it is impossible to assess the validity of this effect (G P Guaraldi et al, Annals of Clinical Psychiatry 1993; 5: 101–5). In alcoholics with depression, 90,000 microg/day of MTHF also produced a reduction in depression in an open study (C Di Palma et al, Current Therapeutic Research 1994; 55: 559–568).

Thus, there is no experimental evidence that folic acid itself is able to enhance the effect of any antidepressant other than lithium. Coppen's patent application mentions only lithium, the tricyclics and the MAOIs and does not describe a single SRI or NRI. It specifically advises against using amounts of folic acid in excess of 300 microg/day. There is evidence that too much folic acid may inhibit zinc absorption and in some individuals precipitate epilepsy (D A Bender, Nutritional Biochemistry of the Vitamins, Cambridge University Press, 1992). All other treatment studies have used MTHF at doses of 15,000 microg/day or more. Only one of these (P S A Godfrey et al cited above) involved both tricyclics and MAOIs.

In view of the recent work on requirements for folate, particularly in people with the common variant MTHFR enzyme, it seemed to us that Coppen might not have been correct in emphasising that intakes of folic acid above 300 microg/day were not indicated as adjuvants to antidepressant therapy. Equally, the adverse effects of high folic acid intakes in animals, and the fact that 15,000 microg/day MTHF in humans produces blood folates levels above the limits of the assay, indicate that the very high levels used in most MTHF studies were too much. We therefore felt that there was a reason for seeing whether a folate intake above 300 microg/day, but well below 15,000 microg/day might have beneficial effects in the management of depression, and particularly on the management of depression with SRIs. Because of their relative safety and reasonable efficacy, SRIs have now become the "gold standard" for depression treatment in developed countries. There is some evidence that depressed people who fail to respond to SRIs may have low folate levels (M Fava et al, American Journal of Psychiatry 1997; 154: 426–8). However, only five out of 213 depressed patients were clearly deficient in folate and all five responded to treatment with the SRI fluoxetine, indicating that there is no simple relationship between folic acid deficiency and depression. The authors state "Our findings of an association between low folate level and both melancholic depression and poorer response to antidepressant treatment do not imply causality, however, and are somewhat limited by the potential for confounding relating to the study design".

GENERAL DESCRIPTION OF THE INVENTION

We have now found that in contrast to the picture emerging from the prior art and various studies identified above, useful clinical results in the treatment of depression can be obtained by the combined administration of folic acid and an anti-depressant selected from SRIs and NRIs. These results involve both increased efficacy and reduced side effects.

Thus, according to a first broad feature of the present invention, there is provided a method for the treatment of depression which comprises administering an anti-depressive selected from the class of SRIs and NRIs and characterised by the administration additionally of folic acid or other folate precursor at a rate equivalent to 300 to 5000 micrograms/day of folate, preferably between 300 and 2000 micrograms/day.

The source of folate may be folic acid, MTHF or other convenient pharmaceutically administrable folate source.

The SRI or NRI may be any of the available ones, or ones which may become available in the future, and should be administered in accordance with the normal prescribed dosage rates. Combinations of SRIs or NRIs or of one or more of each may also be used, though whether any will produce particularly enhanced effects must await the results of clinical trials if attempted.

By way of example, any of the following SRIs or NRIs may be used. These are set out in tabular form together with the usual daily dose and the standard tablet sizes. All of the daily dose and tablet size figures are given in milligrams:

| NRI/SRI Common Name | Usual Daily Dose (mg) | Usual Tablet Content (mg) |
|---|---|---|
| Fluoxetine | 20–80 | 20, 60 |
| Fluvoxamine | 100–300 | 50, 100 |
| Paroxetine | 20–60 | 20, 30 |
| Sertraline | 50–200 | 50, 100 |
| Citalopram | 20–60 | 10, 20 |
| Venlafaxine | 50–400 | 75, 150 |
| Nefazodone | 200–600 | 50, 100, 200 |
| Trazodone | 150–600 | 50, 100, 150 |
| Reboxetine | 4–12 | 4 |

In accordance with a further feature of the invention, there is provided a pharmaceutical dosage form of an anti-depressant containing a quantity of SRI or NRI and a quantity of folic acid or other folate precursor such that the administration of from 1 to 8 units, usually from 1 to 4 units, of the dosage form will provide a dose of the NRI or SRI equivalent to the usually prescribed daily dose thereof and 300 to 5000 micrograms of folate.

Expressed another way, the present invention provides for the treatment of depression, the use of an NRI or SRI administered simultaneously with folate at a dosage of 300 to 5000 micrograms per day and pharmaceutical preparations in any appropriate pharmaceutically acceptable form to provide such therapy. While the present invention is of value in the treatment of depression generally, it is of particular value in the case of the treatment of depression in patients with, or at risk of, cardiovascular disease. It is also of particular value in reducing adverse events associated with treatment.

Specific application of the invention

We have carried out a pilot study which has clearly demonstrated the benefits of the combined administration of folate and an SRI/NRI in accordance with our invention. The study details and results are as follows:

PILOT STUDY 127 patients who fulfilled DSM-IV (Diagnostic and Statistical Manual of Mental Disorders, 4th edition) criteria for major depressive disorder, and who also scored at least 20 on the Hamilton 17-item Depression Rating Scale (HDRS) were entered into the study. All were treated with fluoxetine, the most widely prescribed SRI, and all were randomised on a double blind basis to receive either 500 microg/day folic acid or an identical matching placebo. The idea was to give folic acid at more than double the US Recommended Daily Allowance and 66% above the top end of the range (300 microg/day) recommended by Coppen in 1980. All patients were given a dose of 20 mg fluoxetine/day. Patients were studied for 10 weeks and were assessed on the Hamilton scale at baseline 2, 4, 6 and 10 weeks. Blood samples were taken for measurement of folic acid and of homocysteine at baseline and 10 weeks. The results of the study are shown in Table 1.

It can be seen that improvement in the Hamilton score occurred in both groups but that from week 4 onwards, the improvement was always greater in the folate group and that the difference reached significance at week 10 when the mean improvement in score was 69.8% in the folic group and 59.7% in the placebo group. There were no adverse effects of folic acid and, in particular, there were no epileptic attacks. As expected, blood folic acid substantially increased and homocysteine fell in the folic group, whereas in the placebo group, the levels were unchanged. The differences at 10 weeks between the groups in change in folic acid and change in homocysteine concentrations were statistically highly significant. Since elevated homocysteine is now recognised as a major risk factor for cardiovascular disease, the results indicate that the combination of an SRI with folic acid is of particular value in depressed patients who have or who are at risk of cardiovascular disease, e.g., because of elevated cholesterol, triglyceride levels or raised blood pressure.

The results can be looked at in another way by comparing the two groups with respect to the numbers of patients at 10 weeks showing a 50% improvement from baseline in the HDRS, or by comparing the numbers who remained with HDRS scores above 20, indicating that they would still meet the HDRS criterion for entry into an antidepressant trial. These figures are shown below:

| Numbers showing percentage changes in HDRS from baseline above and below 60% | | |
|---|---|---|
| | Below 50% | Above 50% |
| Folic acid | 14.3% | 85.7% |
| Placebo | 33.3% | 66.7% |
| $x^2 = 3.98$ | | $p < 0.05$ |

| Numbers with HDRS scores below and above 20 at week 10 | | |
|---|---|---|
| | Below 20 | Above 20 |

TABLE 1

Changes of Hamilton Depression Rating Scale, blood folate and blood hemocysteine levels over 10 weeks. All Figures are means, ±SD. Folate is expressed as microg/l and homocysteine as micromul/l ± SD.

| | WEEKS OF STUDY | | | | |
|---|---|---|---|---|---|
| | 0 | 2 | 4 | 6 | 10 |
| Folate - HDRS | 26.0 ± 5.0 | 20.3 ± 5.3 | 14.5 ± 5.8 | 11.6 ± 6.1 | 8.1 ± 5.4 |
| % change from 0 | 0.0 | −24.3% | −46.1% | −56.8% | −69.8% |
| Placebo - HDRS | 26.6 ± 4.7 | 20.1 ± 5.9 | 16.2 ± 7.2 | 12.8 ± 7.4 | 10.7 ± 7.3 |
| % change from 0 | 0.0 | −24.3% | −39.2% | −52.0% | −59.7% |
| Significance of difference | NS | NS | NS | NS | <0.05 |
| Folate - serum folate | 4.5 ± 1.8 | — | — | — | 11.8 ± 1.8 |
| % change | 0.0% | | | | +262.2% |
| Placebo - serum folate | 4.1 ± 1.4 | — | — | — | 4.1 ± 1.3 |
| % change | 0.0% | | | | 0.0% |
| Significance of difference | ns | | | | <0.001 |
| Folate - serum homocysteine | 9.5 ± 3.2 | — | — | — | 8.0 ± 2.2 |
| % change | 0.0 | | | | −10.5% |
| Placebo - serum homocysteine | 9.1 ± 2.8 | — | — | — | 9.7 ± 4.2 |
| % change | 0.0 | | | | +6.5% |
| Significance of difference | NS | — | — | — | <0.01 |

-continued

| Folic acid | 95.9% | 4.1% |
|---|---|---|
| Placebo | 80.4% | 19.6% |
| $x^2 = 4.33$ | | $p < 0.05$ |

Thus, 85.7% of patients on folic acid achieved a greater than 50% improvement as compared to only 66.7% on placebo. 4.1% of patients on folic acid by 10 weeks remained severely depressed enough to fulfil the entry criteria for the trial as compared to 19.6% of patients on placebo.

These results are both statistically significant and clinically important and show that 500 microg/day folic acid can substantially improve the response rate to fluoxetine which is the most widely prescribed SRI. Since the SRIs all have similar mechanisms of action, all SRIs will have their responses to treatment enhanced by the addition of folic acid. The main SRIs known at present are set out above, but this effect will be present with any compound which has an SRI action. NRIs will also respond to folate since it is required for the synthesis of noradrenaline.

The dose of folic acid used in this study was 500 microg/day. Since the active form of folic acid in the body is MTHF, either folic acid or MTHF or any folic acid precursor could be used interchangeably. Folic acid is relatively safe, although physiological doses may possibly enhance the risk of epileptic attacks in those who are susceptible, and many interfere with zinc absorption, while higher doses may interfere with neurotransmitter functions. Doses of above 5000 microg/day are unlikely to produce beneficial effects greater than those found in our study and may well produce adverse effects.

A further feature which emerged from the pilot study was the substantial and surprising drop in adverse reaction reports. 65 patients in the fluoxetine+placebo group reported 98 adverse events, or 1.51/patient. 62 patients in the fluoxetine+folic group reported 53 adverse events or 0.85/patient. This difference was highly significant at $p<0.01$. The adverse events were typical of these reported for SRIs and mostly consisted of fatigue, nausea and dizziness. This 44% reduction in adverse events is of very great clinical benefit. It was a wholly unexpected outcome of the study.

In accordance with the invention, folate or MTHF supplements are used as adjuvants to drugs with SRI action in the treatment of depression, with a daily dose of folic acid in dosage forms which deliver 300 to 5000 microg/day, and preferably 300 to 2000 microg/day. In the treatment of all psychiatric disorders, including depression, compliance with the drug treatment regime prescribed is a major problem. Patients are too lethargic, or forget or are simply resistant to taking their therapy. For this reason, it is important to make the treatment regimes as simple as possible. The ideal, therefore, is to incorporate the folic acid or MTHF into the same tablet, capsules or liquid preparation which contains the SRI. One way of doing this is to incorporate 300–2000 microg of folate into the starting daily dose form of the drug. Patients would therefore automatically take in an appropriate level of folate. If drug dosage has to be increased, the top daily dose is not usually more than 4 times the starting daily dose for this class of compounds. The top dose of folate used would thus be well within the likely safe range. It is possible that treatment-resistant patients may have unusually low folate levels or have the variant in the MTHFR enzyme which means that they have a higher requirement for folate. Such patients would therefore automatically receive an increased intake of folate as their SRI dose was increased.

Because depression is associated with an increased risk of cardiac disease, and because both depression and cardiac disease are associated with elevated homocysteine and reduced folate levels in some patients, this combination of SRIs with folate is of particular value in the many patients who are both depressed and who have cardiovascular diseases such as coronary artery disease, peripheral artery disease, angina, myocardial infarction, transient ischaemic attacks, stroke or hypertension, or who have elevated levels of risk factors such as total cholesterol, LDL-cholesterol or triglycerides. A particular indication for the folic acid/SRI combination is therefore depression in association with cardiovascular disease or cardiovascular risk of any type.

SPECIFIC EXAMPLES OF PREFERRED FORMULATIONS

The following are given as typical examples of formulations according to the present invention.

Example 1

20 mg of fluoxetine formulated as a tablet, as a capsule or in a liquid dosage form such as a solution or an emulsion, with between 300 and 1000 microg of folic acid, preferable 400 to 600 microg, incorporated into the 20 mg tablet or other dosage form.

Example 2

100 mg of fluvoxamine formulated as a tablet, as a capsule or in a liquid dosage form such as a solution or an emulsion, with between 300 and 1000 microg of folic acid, preferable 400 to 600 microg, incorporated into the 100 mg tablet or other dosage form.

Example 3

20 mg of paroxetine formulated as a tablet, as a capsule or in a liquid dosage form such as a solution or an emulsion, with between 300 and 1000 microg of folic acid, preferable 400 to 600 microg, incorporated into the 20 mg tablet or other dosage form.

Example 4

50 mg of sertraline formulated as a tablet, as a capsule or in a liquid dosage form such as a solution or an emulsion, with between 300 and 1000 microg of folic acid, preferable 400 to 600 microg, incorporated into the 50 mg tablet or other dosage form.

Example 5

10 mg of citalopram formulated as a tablet, as a capsule or in a liquid dosage form such as a solution or an emulsion, with between 300 and 1000 microg or folic acid, preferable 400 to 600 microg, incorporated into the 10 mg tablet or other dosage form.

Example 6

75 mg of venlafaxine formulated as a tablet, as a capsule or in a liquid dosage form such as a solution or an emulsion, with between 300 and 1000 microg of folic acid, preferable 400 to 600 microg, incorporated into the 75 mg tablet or other dosage form.

Example 7

100 mg of nefazodone formulated as a tablet, as a capsule or in a liquid dosage form such as a solution or an emulsion, with between 300 and 1000 microg of folic acid, preferable 400 to 600 microg, incorporated into the 100 mg tablet or other dosage form.

Example 8

100 mg of trazodone formulated as a tablet, as a capsule or in a liquid dosage form such as a solution or an emulsion, with between 300 to 1000 microg of folic acid, preferable 400 to 600 microg, incorporated into the 100 mg tablet or other dosage form.

Example 9

4 mg of reboxetine formulated as a tablet, as a capsule or in a liquid dosage form such as a solution or an emulsion, with between 300 and 1000 microg of folic acid, preferable 400 to 600 microg, incorporated into the 4 mg tablet or other dosage form.

Example 10

The starting daily dose of any other SRI formulated as a tablet, as a capsule or in a liquid dosage form such as a solution or an emulsion, with between 300 and 1000 microg of folic acid, preferable 400 to 600 microg, incorporated into the dosage form.

Example 11

The starting daily dose of any noradrenaline reuptake inhibitor as a tablet, as a capsule or in a liquid dosage form such as a solution or an emulsion, with between 300 and 1000 microg of folic acid, preferable 400 to 600 microg, incorporated into the dosage form.

We claim:

1. A method of treating depression in a patient in need of such treatment comprising administering to the patient a therapeutically effective amount of an anti-depressive compound selected from the class of compounds comprising serotonin reuptake inhibitors and noradrenaline reuptake inhibitors, in combination with a folate source selected from folic acid and folate precursors, wherein the administration of the folate source provides from 300 to 5,000 micrograms per day folate.

2. The method of claim 1 wherein the administration of the folate source provides from 300 to 2,000 micrograms per day folate.

3. The method of claim 1 wherein the source of folate is folic acid.

4. The method of claim 1 wherein the source of folate is methyltetrahydrofolic acid.

5. A method of treating depression in a patient in need of such treatment comprising administering to the patient a therapeutically effective amount of an anti-depressive compound selected from fluoxetine, fluvoxamine, paroxetine, sertraline, citalopram, venlafaxine, nefazodone, trazodone and reboxetine, in combination with a compound selected from folic acid and methyltetrahydrofolate, wherein the rate equivalent administration of folic acid and methyltetrahydrofolate provides from 300 to 5,000 micrograms per day folate.

6. A method of reducing the side effects of depression in a patient in need of such treatment comprising administering to the patient a therapeutically effective amount of an anti-depressive compound selected from the class of compounds comprising serotonin reuptake inhibitors and noradrenaline reuptake inhibitors, in combination with a folate source selected from folic acid and folate precursors, wherein the administration of the folate source provides from 300 to 5,000 micrograms per day folate.

7. The method of claim 6, wherein the anti-depressive compound is selected from fluoxetine, fluvoxamine, paroxetine sertraline, citalopram, venlafaxine, nefazodone, trazodone and reboxetine.

8. A method of treating depression in a patient in need of such treatment comprising administering to the patient a therapeutically effective amount of an anti-depressive compound selected from the class of compounds comprising serotonin reuptake inhibitors and noradrenaline reuptake inhibitors, in combination with a folate source selected from folic acid and folate precursor, wherein the patient has cardiovascular disease or is at risk of developing cardiovascular disease.

9. A method of treating depression in a patient in need of such treatment comprising administering to the patient a therapeutically effective amount of a noradrenaline reuptake inhibitor simultaneously with a folate source at a dosage of 300 to 5,000 micrograms per day folate.

10. A method of treating depression in a patient in need of such treatment comprising administering to the patient a therapeutically effective amount of a serotonin reuptake inhibitor simultaneously with a folate source at a dosage of 300 to 5,000 micrograms per day folate.

11. A pharmaceutical composition comprising an anti-depressive compound selected from the class of compounds comprising serotonin reuptake inhibitors and noradrenaline reuptake inhibitors, and a folate source selected from folic acid and folate precursors, wherein 1 to 8 units of the composition contains the anti-depressive compound in a therapeutically effective a mount and the folate source provides from 300 to 5,000 micrograms per day folate.

* * * * *